(12) United States Patent
Iaquaniello et al.

(10) Patent No.: US 9,394,219 B2
(45) Date of Patent: Jul. 19, 2016

(54) METHOD FOR PRODUCING SYNTHESIS GAS FOR METHANOL PRODUCTION

(71) Applicant: STAMICARBON B.V., Sittard (NL)

(72) Inventors: Gaetano Iaquaniello, Rome (IT); Barbara Cucchiella, Rome (IT); Elena Antonetti, Rome (IT)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 14/354,531

(22) PCT Filed: Oct. 25, 2012

(86) PCT No.: PCT/NL2012/050744
§ 371 (c)(1),
(2) Date: Apr. 25, 2014

(87) PCT Pub. No.: WO2013/062413
PCT Pub. Date: May 2, 2013

(65) Prior Publication Data
US 2014/0256994 A1    Sep. 11, 2014

(30) Foreign Application Priority Data
Oct. 26, 2011    (EP) .................................. 11186753

(51) Int. Cl.
| | | |
|---|---|---|
| *C07C 29/48* | (2006.01) | |
| *C01B 3/38* | (2006.01) | |
| *C01B 3/48* | (2006.01) | |
| *C07C 29/151* | (2006.01) | |
| *C01B 3/32* | (2006.01) | |

(52) U.S. Cl.
CPC .................. *C07C 29/48* (2013.01); *C01B 3/323* (2013.01); *C01B 3/386* (2013.01); *C01B 3/48* (2013.01); *C07C 29/1518* (2013.01); *C01B 2203/0261* (2013.01); *C01B 2203/0283* (2013.01); *C01B 2203/043* (2013.01); *C01B 2203/0475* (2013.01); *C01B 2203/061* (2013.01); *C01B 2203/1235* (2013.01); *C01B 2203/1258* (2013.01); *C01B 2203/142* (2013.01)

(58) Field of Classification Search
None
See application file for complete search history.

(56) References Cited

U.S. PATENT DOCUMENTS

| | | | |
|---|---|---|---|
| 5,252,609 A | 10/1993 | Pinto | |
| 2004/0101473 A1* | 5/2004 | Wang et al. | ............. 423/651 |

FOREIGN PATENT DOCUMENTS

| | | |
|---|---|---|
| EP | 0 233 076 | 8/1987 |
| EP | 640559 | 3/1995 |
| EP | 1 219 566 | 7/2002 |
| WO | WO-00/00426 | 1/2000 |
| WO | WO-01/32556 | 5/2001 |
| WO | WO-01/36323 | 5/2001 |
| WO | WO-03/106393 | 12/2003 |
| WO | WO-2004/083342 | 9/2004 |

OTHER PUBLICATIONS

International Search Report for PCT/NL2012/050744, mailed Feb. 4, 2013, 3 pages.
Basini et al., "Catalytic partial oxidation of natural gas at elevated pressure and low residence time," Catalysis Today (2001) 64(1-2):9-20.
Basini, "Fuel rich catalytic combustion: Principles and technological developments in short contact time (SCT) catalytic processes," Catalysis Today (2006) 117(4):384-393.
Hickman and Schmidt, "Production of syngas by direct catalytic oxidation of methane," Science (1993) 259(5093):343-346.
Hickman and Schmidt, "Synthesis gas formation by direct oxidation of methane over Pt monoliths," J Catalysis (1992) 138(1):267-282.

* cited by examiner

*Primary Examiner* — Scarlett Goon
*Assistant Examiner* — Ana Z Muresan
(74) *Attorney, Agent, or Firm* — Morrison & Foerster LLP

(57) ABSTRACT

Method for producing synthesis gas for methanol production The present invention relates to a method for producing synthesis gas from a hydrocarbon containing feed, which synthesis gas is particularly suitable for subsequent use in methanol production. In this method, a hydrocarbon containing feed, particularly natural gas (100), is subjected to catalytic partial oxidation (CPO) (2), followed by the water gas shift (WGS) (4) reaction of a part of the reformed feed. At least part of the shifted feed is then subjected to hydrogen purification, preferably by pressure swing adsorption (PSA) (5) to obtain pure hydrogen (108), which hydrogen is subsequently combined with the remaining parts of the feeds to yield synthesis gas particularly suitable for methanol synthesis. The recombined stream preferably has an R ratio, being the molar ratio $(H_2-CO_2)/(CO+CO_2)$, in the range 1.9-2.2 and preferably about 2. The invention further relates to a method for producing methanol from a hydrocarbon containing feed, wherein first synthesis gas is obtained according to the method of the invention, which synthesis gas is further used to produce methanol.

9 Claims, 1 Drawing Sheet

METHOD FOR PRODUCING SYNTHESIS GAS FOR METHANOL PRODUCTION

CROSS-REFERENCE TO RELATED APPLICATIONS

This application is the national phase of PCT application PCT/NL2012/050744 having an international filing date of 25 Oct. 2012, which claims benefit of European patent application No. 11186753.7 filed 26 Oct. 2011. The contents of the above patent applications are incorporated by reference herein in their entirety.

FIELD OF THE INVENTION

The present invention relates to synthesis gas production from light hydrocarbons such as natural gas. In particular, the present invention relates to the production of synthesis gas particularly suitable for methanol production.

BACKGROUND OF THE INVENTION

Commercial methanol plants produce methanol in several steps, usually including synthesis gas preparation (reforming), methanol synthesis and methanol purification. Since these steps are conducted in separate process sections, the technology for each section can be selected and optimised independently. The usual criteria for the selection of technology are capital cost and plant efficiency. The preparation of synthesis gas and compression typically accounts for about 60% of the total investment, and almost all energy is consumed in this process section. Therefore, the technology to produce synthesis gas is of major importance.

The synthesis gas for the production of methanol is usually obtained by subjecting a desulfurised hydrocarbon feed to steam reforming (SR) at a temperature from 800 to 950° C. in the presence of a fixed bed of catalyst, typically containing nickel. The resulting synthesis gas is cooled and compressed to be used further in the methanol process. However, the synthesis gas obtained in steam reforming is usually characterised by a too low carbon/hydrogen ratio compared to a stoichiometric composition optimal for methanol synthesis. As a result, the methanol synthesis reactor typically operates at a large hydrogen excess which results in the overall low plant efficiency.

To adjust the composition of the synthesis gas used for methanol production, a combination of technologies can be used. A method for methanol production known as Combined Reforming Technology (CRT) is described in EP 0233076. Herein, a hydrocarbon feed is split into two feedstock fractions, of which one fraction is subjected to primary steam reforming and is then combined with the second feedstock fraction. The resulting mixture is reacted with an oxygen containing gas in a secondary reforming reactor. The resulting raw synthesis gas is mixed with a hydrogen-rich stream obtained from the purge gas from a methanol synthesis loop, which final mixture is then fed to the synthesis loop for methanol production. In order to achieve a stoichiometric ratio of hydrogen to carbon oxides, up to 50-60% of the entire feed needs to be subjected to steam reforming. This makes the steam reforming section of a methanol plant a considerable fraction of the investment of the entire plant. In addition, high steam reforming duty is also associated with significant fuel consumption by external burners in order to maintain the high temperatures required during steam reforming. This, in turn, leads to high $CO_2$ emissions into the atmosphere.

It is therefore desired to provide a method for producing synthesis gas for methanol production, which process would be substantially devoid of the above disadvantages. Particularly, it is desired to have a process with a reduced fuel consumption and a reduced $CO_2$ emission while producing synthesis gas having an optimal components ratio for methanol production.

SUMMARY OF THE INVENTION

In order to better address one or more of the foregoing desires, the invention presents, in one aspect, a method for producing synthesis gas from a hydrocarbon containing feed, comprising the steps of:
 (i) subjecting the hydrocarbon containing feed to catalytic partial oxidation (CPO) yielding a first gas mixture,
 (ii) subjecting part of the first gas mixture to a water gas shift (WGS) reaction yielding a second gas mixture, the untreated part being a first remaining gas mixture,
 (iii) subjecting at least part of the second gas mixture to hydrogen purification, preferably by pressure swing adsorption (PSA), yielding a hydrogen containing gas mixture, the untreated part, if present, being a second remaining gas mixture,
 (iv) combining at least part of the hydrogen containing gas mixture with the first and, if present, the second remaining gas mixtures to yield synthesis gas for methanol synthesis.

The invention, in another aspect, provides a method for producing methanol from a hydrocarbon containing feed comprising the steps according to the invention to obtain a synthesis gas, and using said synthesis gas to produce methanol.

DETAILED DESCRIPTION OF THE INVENTION

Figure 1:
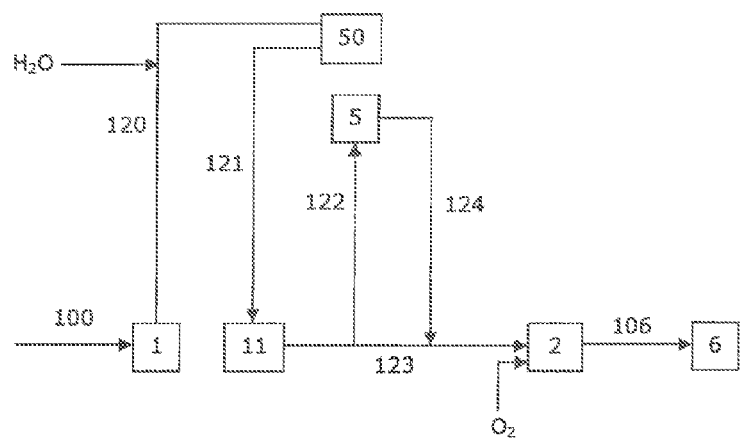
FIG. 1 schematically shows a conventional method wherein use is made of a combined reformer with a pre-reforming section.

The present invention provides a method for producing synthesis gas, which synthesis gas is particularly suitable for use in methanol production. As used herein, a synthesis gas suitable for methanol production means that the synthesis gas has a certain ratio of components, especially of hydrogen and carbon oxides, which is optimal for methanol synthesis. In particular, methanol synthesis gas can be characterised by a molar ratio $(H_2-CO_2)/(CO+CO_2)$, referred to herein as an R ratio. An R ratio equal to 2 corresponds to a stoichiometric synthesis gas for formation of methanol. The synthesis gas obtained according to the method of the present invention has preferably an R ratio in the range of 1.90-2.20, more preferably 1.95-2.05.

According to the present invention, a hydrocarbon containing feed is provided. Any hydrocarbon containing feed suitable for steam reforming can be used. Preferably, the feed contains light hydrocarbons such as $C_{1-4}$ alkanes, e.g. methane, ethane, etc. More preferably, the feed contains methane or a gas containing substantial amounts of methane, preferably natural gas. It is preferred to use a desulfurised feed. Therefore, if needed, the hydrocarbon containing feed can be subjected to a desulfurisation step.

The hydrocarbon containing feed is subjected to catalytic partial oxidation (CPO). This typically involves a reaction of hydrocarbons with steam and oxygen in the presence of a catalyst. In case of natural gas or other methane containing feed, the reaction can be represented as follows:

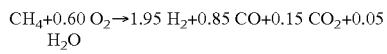

$$CH_4 + 0.60\ O_2 \rightarrow 1.95\ H_2 + 0.85\ CO + 0.15\ CO_2 + 0.05\ H_2O$$

In this reaction, the R ratio of the product is typically 1.87. The reaction is typically performed in the presence of a metal catalyst. The catalytic metal is preferably a Group VIII noble metal, e.g., platinum, iridium, rhodium, osmium, ruthenium, although nickel may also be used as the catalytic metal. The oxygen used in the catalytic partial oxidation process may be pure or substantially pure oxygen or an oxygen containing gas, e.g., air, or a mixture of oxygen with an inert gas. Substantially pure oxygen (that is, containing more than 99% oxygen) is particularly preferred, and pure oxygen containing more than 99.9% oxygen is still more preferred.

Prior to the CPO reaction, the hydrocarbon containing feed, or at least part of it, is preferably subjected to pre-reforming. Where "part of a feed" is mentioned, it is understood to encompass more than 0% but less than 100% of the feed, hence not including the end points "0%" and "100%". For example, the part can be 0.1-99.9%, or 1-99% of the feed, or any other value not being 0% and 100%. In a pre-reformer, higher hydrocarbons (higher than $C_1$) are converted into methane, which makes the feed more uniform. Another advantage is that oxygen consumption in the CPO reactor is thereby minimised. Adiabatic steam reforming can be used for pre-reforming. In the pre-reforming the steam-to-carbon molar ratio is preferably from 1.5 to 2, more preferably from 1.6 to 1.7.

To ensure a particularly effective conversion in the pre-reforming, the feed can be preheated to the pre-reforming temperature which is, preferably, in the range of 250-600° C., more preferably 450-550° C. and in particular about 475° C. To preheat the pre-reforming feed, the heat of process streams elsewhere in the system can be used. For example, the pre-heating can conveniently be done by exchanging heat with a stream leaving a process gas boiler. In a process gas boiler, a high-temperature stream leaving the CPO reactor is cooled down and can be used to preheat the pre-reforming feed in a gas-gas exchanger.

The feed supplied to the CPO reactor is preferably pre-heated to a temperature of 200-500° C., preferably 350-450° C. and in particular to a temperature of about 400° C. At these temperatures, the supply of oxygen to the CPO reactor is minimised. This also reduces the costs for the air separation unit (ASU), in case the latter is used to supply oxygen for the CPO reaction. The hydrocarbon containing feed and the oxygen can be in various ratios in the feed gas mixture. The precise mixture introduced into the reaction zone depends on the particular hydrocarbons used and the amount of oxygen necessary to conduct the partial oxidation reaction. Operable ratios can be easily determined by one skilled in the art. Usually, the $O_2/C$ (Oxygen to Carbon) ratio is in the range 0.4-0.6, preferably about 0.5.

The term CPO (also often referred to as SCT-CPO) is known to the skilled person. SCT-CPO refers to Short Contact Time Catalytic Partial Oxidation. The CPO reaction takes place in a reactor under the influence of a catalyst at residence times between $10^{-2}$ to $10^{-4}$ and with typical catalyst surface contact times around $10^{-6}\ s^{-1}$. These contact time correspond to typical space velocities of 100,000 to 250,000 $hr^{-1}$, preferably 100,000 to 200,000 $hr^{-1}$. Catalysts employed for SCT-CPO comprise Ni, Pd, Pt, Rh, or Ru. The reaction takes place at catalyst surface temperatures above 950° C., preferably above 1000° C. By employing said short contact times and high catalyst surface temperatures the formation of CO is highly favoured and the formation of carbon or CO2 is suppressed. This leads to a highly favourable synthesis gas composition. A reference to CPO is (a) L. Basini, Catalysis Today 117 (2006) 384-393. Other references include (b) L. Basini, K. Aasberg-Petersen, A. Guarinoni, M. Oestberg, Catalysis Today (2001) 64, 9-20 "Catalytic Partial Oxidation of Natural Gas at Elevated Pressure and Low Residence Time"; (c) H. Hickman, L. D. Schmidt, J. Catal. 138 (1992) 267; (d) D. Hichman, L. D. Schmidt Science, 259 (1993) 343; (e) L. Basini, G. Donati WO 97/37929; (f) Sanfilippo, Domenico; Basini, Luca; Marchionna, Mario; EP-640559; (g) D. Schaddenhorst, R. J. Schoonebeek; WO 00/00426; (h) K. L. Hohn, L. D. Schmidt, S. Reyes, J. S. Freeley, WO 01/32556; (i) A. M. Gaffney, R. Songer, R. Ostwald, D. Corbin, WO 01/36323.

As a result of the CPO reaction, a first gas mixture comprising hydrogen ($H_2$), carbon monoxide (CO) and carbon dioxide ($CO_2$) is formed. The mixture is preferably cooled in a process gas boiler and then divided into two streams. In a preferred embodiment, the first gas mixture after the CPO process contains less carbon dioxide than in a conventional CRT process. This is particularly advantageous in methanol plants, which require a $CO_2$ content as low as possible. Preferably, the first gas mixture comprises less than 10 vol. % $CO_2$ on dry basis, more preferably less than 6 vol. % $CO_2$ on dry basis. The $CO/CO_2$ ratio of the first gas mixture is preferably from 5 to 15, and more preferably about 10.

Part of the first gas mixture is then subjected to a water gas shift (WGS) reaction to adjust the $CO/CO_2$ ratio of the gas mixture, the untreated part being a first remaining gas mixture. In the WGS reaction, carbon monoxide together with extra steam is converted to additional hydrogen and carbon dioxide, yielding a second gas mixture. During the WGS reaction, the $CO/CO_2$ ratio is preferably reduced to a value 3 to 10, more preferably to a value from 6 to 7. By modifying the amount of gas by-passing the WGS reactor, the $CO/CO_2$ ratio can conveniently be adjusted.

At least part of the second gas mixture originating from the WGS reaction is further subjected to hydrogen purification, preferably by pressure swing adsorption (PSA), to separate $CO_2$ and obtain a hydrogen containing gas mixture. Preferably, part of the second mixture is subject to hydrogen purification, that is up to but not including 100 vol. %. The untreated part of the second gas mixture if present) is referred to herein as a second remaining gas mixture. Preferably, pure hydrogen with a purity higher than 99% is obtained. The purge gas obtained during hydrogen purification, e.g. in a PSA unit, can suitably be supplied to the CPO reactor or added to the hydrocarbon containing feed before the desulfurisation step.

In a further step, the unshifted part of the first gas mixture (first remaining gas mixture) is combined with the part of the second gas mixture not subjected to hydrogen purification (second remaining gas mixture), if present, and with at least part of the hydrogen obtained during hydrogen purification, to obtain a synthesis gas particularly suitable for methanol synthesis. By combining said the at least two, but preferably three mentioned gas streams, the composition of the gas obtained in the CPO reaction is first adjusted with respect to the $CO/CO_2$ ratio through the WGS reaction and then with respect to the $H_2/CO$ ratio by the addition of pure hydrogen. Preferably, the R ratio of the synthesis gas is raised in this way to above 1.9, and preferably to about 2.

The part of the reformed feed (first gas mixture) that is branched off for the WGS reaction may be chosen based on the feed composition and on the subsequent application of the synthesis gas, particularly methanol synthesis. It is preferred to use up to 50 vol. % of the feed in the WGS reaction, such as from 5 to 50 vol. %, more preferably from 10 to 40 vol. %. In an alternative embodiment, 5 to 20 vol. % of the first gas mixture is subjected to the WGS reaction. Preferably 20-100 vol. % of the shifted feed (second gas mixture), more preferably from 20 up to but not including 100 vol. %, is further subjected to hydrogen purification, preferably, by PSA. In a preferred embodiment, 40-80 vol. % is subjected to hydrogen purification, such as 50-70 vol. %.

When the final synthesis gas is used for methanol production, it is particularly advantageous to subject 5 to 15 vol. % of the first gas mixture to the WGS reaction and 40 to 60 vol. % of the second gas mixture to hydrogen purification. A particularly preferred embodiment includes about 10 vol. % and about 50 vol. % of the respective feeds. However, to accommodate different $H_2/CO$ and $CO/CO_2$ ratios, the proportions of different feeds can be varied in broad ranges, such as, for example, from 5 to 50 vol. % of the first gas mixture subjected to the WGS reaction, in combination with 50-100 vol. % of the second gas mixture subjected to hydrogen purification.

In another aspect, the present invention relates to a method for producing methanol from a hydrocarbon containing feed. The method comprises the steps previously described to obtain a synthesis gas, which synthesis gas is then used to produce methanol. Any suitable method to produce methanol from synthesis gas can be used. Typically, carbon oxides and hydrogen from the synthesis gas react on a catalyst to produce methanol. The catalyst for this reaction usually contains copper and zinc.

Using a CPO reaction to produce synthesis gas makes it possible to keep the $CO_2$ content lower than in the conventional technology. This is particularly advantageous for the plants where the $CO_2$ amount is required to be limited. Moreover, a high $CO/CO_2$ ratio during the methanol synthesis increases the reaction rate and conversion and also decreases the water formation, which in turn reduces the catalyst deactivation rate.

The process according to the invention presents several advantages, one of which is the flexibility of using different feedstocks as to their composition. The present method allows different sources of carbonaceous material to be used, e.g. natural gas or naphta, but also different sources of natural gas varying from high caloric value natural gas to low caloric value natural gas. The different feedstocks lead to a different composition of the reaction products, which, in turn, leads to a deviation from the optimal ratios of $H_2/CO$ and $CO/CO_2$. This is particularly a problem when a pre-reformer is not present. These ratios, however, may suitably be adjusted by applying the method of the present invention, to arrive to a desired product composition.

Another advantage is associated with the startup of the process, when the optimum temperature of the reaction is not yet reached and the product composition deviates from the desired composition. Since the composition of the end product can easily be varied by varying the ratio of different gas streams, the process of the invention allows a quicker startup of the production of any downstream processes e.g. methanol production.

Yet a further advantage is that by applying the method of the invention, the economy of synthesis gas production is improved. The method results in a reduction of costs, e.g., because it allows to produce syngas with a desired composition without the need to install expensive process units such as a steam reformer (SR) and an autothermal reformer (ATR), as conventionally used in the prior art. Moreover, the invention allows to produce synthesis gas for methanol production with a negligible or even zero $CO_2$ emission into the atmosphere.

The present invention will further be described with respect to particular embodiments and with reference to certain drawings but the invention is not limited thereto but only by the claims Any reference signs in the claims shall not be construed as limiting the scope. If not specifically indicated, all percentages for gases are given by volume. The drawings described are only schematic and non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

FIG. 1 illustrates a known combined technology process. In this process, a natural gas feed 100 is desulfurised in a hydrodesulfurisation (HDS) reactor 1. A desulfurised feed 120 is then subjected to preheating in a convection section 50 of a steam reformer (SR) 5. Preheated stream 121 is mixed with steam and supplied to a pre-reformer 11, whereafter the stream is split into two feed streams, 122 and 123. Stream 122 is supplied to the steam reformer 5, in which natural gas together with steam is catalytically converted to a synthesis gas 124. Stream 123 is mixed with synthesis gas 124 and both are fed into an autothermal reformer (ATR) 2. In the ATR, the mixed gas stream together with oxygen is reformed to a synthesis gas 106, which has a proper composition to be used (after compression) for methanol synthesis in a synthesis reactor 6.

Figure 2:
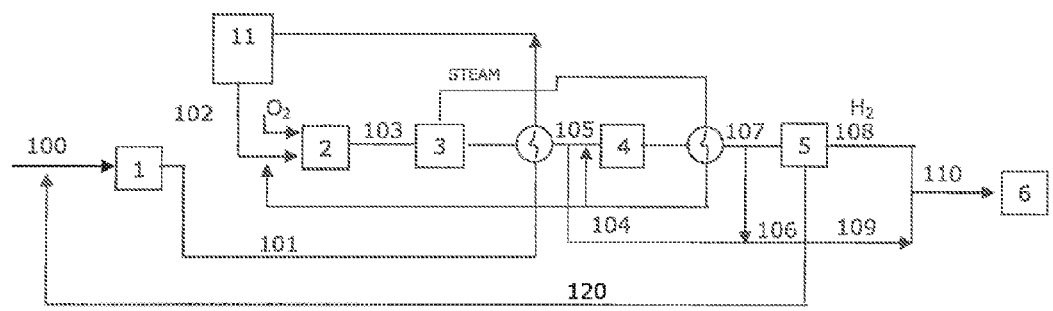
FIG. 2 schematically shows a method according to the invention for the production of synthesis gas for methanol manufacturing with a pre-reforming section.

FIG. 2 shows an embodiment according to the present invention, wherein synthesis gas for methanol production is obtained. In this figure, a natural gas feed 100 is desulfurised in a HDS reactor 1. The feed stream 101 is then preheated using heat exchange with a gas stream of a process gas boiler 3 and introduced, after adding steam, to a pre-reforming section 11. To a partially reformed stream 102 pure oxygen is added to carry out the conversion of the hydrocarbon feed in a CPO reactor 2, resulting in stream 103.

The stream 103 is cooled in the process gas boiler 3, thereby generating steam and split into two streams 104 and 105. First stream 104 by-passes a WGS reactor 4, while the second stream 105 after steam addition is introduced into the WGS reactor 4. The shifted stream is further split into two streams, 106 and 107. Stream 106 is combined with the unshifted stream 104 to form stream 109, while stream 107 is introduced into a PSA unit 5 or equivalent system to get pure or almost pure $H_2$ stream 108 and a purge gas stream 120 which may be sent back to the desulfurisation unit 1 or in an alternative embodiment directly to the CPO reactor.

Stream 108 is then combined with stream 109 to form stream 110, which is a synthesis gas having an $H_2/CO$ ratio equal to 3 and an R ratio $(H_2-CO_2)(CO+CO_2)$ equal to 2, thereby having a particularly suitable composition to enter a methanol production unit 6.

The splitting ratio for streams 104/105 depends on the feed composition, presence of a pre-reforming section and on the specific syngas application. For methanol application using natural gas as feed and a pre-reforming at 475° C. such ratio is preferably 80/20 (vol). The subsequent ratio 106/107 is preferably 50/50 (vol).

In an alternative procedure pre-reforming may be omitted.

The invention claimed is:

1. Method for producing synthesis gas having an optimal components ratio for methanol production from a hydrocarbon containing feed,
comprising the steps of:
   (i) subjecting the hydrocarbon-containing feed to catalytic partial oxidation (CPO) yielding a first gas mixture,
   (ii) subjecting part of the first gas mixture to a water gas shift (WGS) reaction thereby yielding a second gas mixture and an untreated part of said first gas mixture, said untreated part being a first remaining gas mixture,
   (iii) subjecting part of the second gas mixture to hydrogen purification thereby yielding a hydrogen-containing gas mixture and an untreated part of said second gas mixture, said untreated part being a second remaining gas mixture, and
   (iv) combining at least part of the hydrogen containing gas mixture with the first remaining gas mixture and the second remaining gas mixture to yield synthesis gas for methanol synthesis, wherein said synthesis gas for methanol synthesis has an R ratio, which is the molar ratio $(H_2-CO_2)/(CO+CO_2)$, in the range from 1.90 to 2.20 wherein in step (ii) 5 to 50 vol. % of the first gas mixture is subjected to the WGS reaction, and wherein in step (iii) 20-80 vol. % of the second gas mixture is subjected to hydrogen purification.

2. The method according to claim 1, wherein at least part of the hydrocarbon containing feed is subjected to pre-reforming before step (i).

3. The method according to claim 2, wherein the pre-reforming temperature is between 250 and 600° C.

4. The method according to claim 1, wherein the hydrocarbon containing feed is preheated to a temperature from 200 to 500° C. before the CPO reaction in step (i).

5. The method according to claim 1, wherein in step (iii) 20-60 vol. % of the second gas mixture is subjected to hydrogen purification.

6. The method of claim 1, wherein hydrogen purification in step (iii) is by pressure swing adsorption (PSA).

7. The method according to claim 1, wherein 5 to 15 vol. % of the first gas mixture is subjected to the WGS reaction and 40 to 60 vol. % of the second gas mixture is subjected to hydrogen purification.

8. The method according to claim 1, wherein the first gas mixture contains a molar ratio $CO/CO_2$ from 5 to 15.

9. Method for producing methanol from a hydrocarbon containing feed comprising performing the steps according to claim 1 to obtain a synthesis gas, and converting the synthesis gas to produce methanol.

* * * * *